United States Patent
Bancroft

(10) Patent No.: US 7,608,219 B2
(45) Date of Patent: Oct. 27, 2009

(54) STERILIZER TEST DEVICE

(75) Inventor: Richard Bancroft, Leicester (GB)

(73) Assignee: Albert Browne Ltd, Leicester (GB)

( * ) Notice: Subject to any disclaimer, the term of this patent is extended or adjusted under 35 U.S.C. 154(b) by 309 days.

(21) Appl. No.: 10/182,213

(22) PCT Filed: Dec. 18, 2000

(86) PCT No.: PCT/GB00/04873

§ 371 (c)(1),
(2), (4) Date: Oct. 7, 2002

(87) PCT Pub. No.: WO01/56618

PCT Pub. Date: Aug. 9, 2001

(65) Prior Publication Data

US 2003/0133837 A1   Jul. 17, 2003

(30) Foreign Application Priority Data

Feb. 3, 2000   (GB) ................................. 0002382.0

(51) Int. Cl.
*G01N 33/00* (2006.01)
(52) U.S. Cl. ........................................... 422/58; 436/1
(58) Field of Classification Search ............... 422/58; 436/1, 164
See application file for complete search history.

(56) References Cited

U.S. PATENT DOCUMENTS

| | | | | | |
|---|---|---|---|---|---|
| 5,736,355 | A | * | 4/1998 | Dyke et al. | 435/31 |
| 5,830,683 | A | * | 11/1998 | Hendricks et al. | 435/31 |
| 6,406,879 | B2 | * | 6/2002 | James et al. | 435/32 |

FOREIGN PATENT DOCUMENTS

| | | | |
|---|---|---|---|
| EP | 0 419 282 | A | 3/1991 |
| EP | 0 421 760 | A | 4/1991 |
| EP | 0 460 323 | A | 12/1991 |
| GB | 2 180 933 | A | 4/1987 |

* cited by examiner

*Primary Examiner*—Lyle A Alexander
(74) *Attorney, Agent, or Firm*—Nixon Peabody LLP

(57) ABSTRACT

A re-usable sterilizer test device is disclosed which is comprised of at least two parts which are releasably connected together. An indicator device which changes colour in the presence of steam after a certain time period is deposited within the two parts. One or both of the bodies is manufactured from a material having a predetermined degree of porosity as regards steam and is generally cylindrical or spherical so that the outer surface of said one or both bodies forms a significant and substantial portion of the external surface of the assembled device. Steam penetrates the porous body and passes into a cavity inside the body from where the steam can move internally of the device through suitable passageways and into a chamber where the indicator is located.

14 Claims, 2 Drawing Sheets

STERILIZER TEST DEVICE

This invention relates to a sterilizer test device.

Almost all hospitals in the western world are provided with sterilizing equipment to ensure the sterility of instruments and devices which may come into contact with humans. The risks and dangers of conducting operative procedures on living creatures including animals and humans with non-sterile equipment and in non-sterile surroundings is well documented. In an environment in which patients expect to be treated successfully and in a sterile manner, the requirement for effective sterilization is an essential one, and devices have been developed to test the efficacy of sterilizers and sterilization.

Although the following description relates exclusively to the use of sterilizer test devices in hospitals, the device of the present invention has much wider application, and specifically can be used in bench top sterilizers such as might be provided in community healthcare and animal care clinics for the sterilization of utensils, dressings, medical textiles and the like.

Modern sterilizers, many of which are in the form of high pressure autoclaves, subject their contents to high temperature steam for a predetermined period of time. The three fundamental parameters of the sterilization process are accordingly time, temperature, and the presence of steam. Effective sterilization can only be achieved if there is steam contact with all parts of the load to be sterilized for the correct period of time. Air trapped and entrained within the load will prevent this necessary steam penetration. The thermodynamic irregularities of air/water vapour mixtures, and the necessarily hostile environment developed inside cabinet autoclaves makes the monitoring of sterilization process difficult, and therefore a simple visual indicator test was developed.

In the 1960s, the Bowie Dick test assessed whether the air removal stage of the sterilization process was sufficient to ensure rapid and even steam penetration to all parts of the load. The test involved placing within the sterilizer a stack of towels approximately 11 inches high and having a cross-sectional area roughly approximating to the size of an A4 sheet of paper. Within the stack at approximately half height thereof, there was placed a sheet of paper on one surface of which was applied a pattern of a chemical indicator ink which was extremely sensitive to and changed colour in the presence of high temperature steam. The test was performed by simply placing the stack towels within the sterilizer, and initiating a standard cycle of the sterilizer which would be carried out on, for example a tray of surgical instruments, hospital bed linen and the like, for a certain period of time, for example 3-4 minutes. On removal of the stack of towels, the indicator sheet was inspected for a uniform colour change of the indicator over the entire surface of the sheet, and if this was the case then the sterilizer air removal stage was considered to be functioning effectively.

It is well known that heat alone can provide effective sterilization, however the rapid inactivation of microorganisms is significantly faster in the presence of moist heat (steam). For example, effective sterilization can be achieved by subjecting material to dry heat at 160° C. for 1 hour, whereas the same level of sterilization can be achieved by introducing steam at 130° for 3 minutes. In the Bowie Dick test, the towels were used as what is now termed a "porous load". Such loads are deemed one of the most difficult to assess the penetration characteristics of the steam or to provide some resistance to the steam as it progresses towards the indicator sheet. The rationale behind this test is that if the steam can penetrate the porous load to adequately change the colour of the indicator sheet, then any medical device, textile or the like having a lower resistance to steam penetration will be effectively sterilized.

A current modification of the original Bowie & Dick test is the use of a disposable or reusable barrier surrounding a chemical indicator sheet. This is calibrated to perform in a similar manner to the original Bowie & Dick towel pack with a chemical indicator inserted. After the pack has been subjected to a conventional sterilization, the indicator sheet is removed and inspected for a uniform colour change over the entire surface area of the sheet, which is indicative of the effective operation of the sterilizer air removal stage.

A disadvantage with this method of testing is that the product once used must be discarded. When it is considered that millions of tests are conducted annually in hospitals and other sterile environments around the world, the cost saving to be made by a reusable device may be considerable.

One alternative currently available to the disposable test pack described above is a device which comprises a coiled narrow lumen approximately 2-3 metres in length and having a diameter of approximately 2 mm, open at one end and connected at its alternate end to a small accessible capsule into which a chemical indicator can be placed. In use, the coiled lumen is placed inside the sterilizer whereafter the sterilization procedure is initiated during which the steam gradually progresses along the interior of the lumen until reaching the capsule into which the lumen passes. The efficacy of steam penetration can be assessed based on the chemical indicator result. Thereafter, the device may be reused, using a new indicator in the capsule.

The length and narrow entrance of the lumen open end render the lumen arguably not analogous to a porous load for reasons of mass, directional sensitivity, and physical shape etc.

Hence there are a number of serious disadvantages associated with the lumen device. Firstly, the history of use of the device cannot easily be established and although the chemical indicator may be replaced before each use of the device, there is no guarantee that the device was not previously mistreated or was not fully prepared for the next use by the previous user. It is to be borne in mind that in a busy hospital, the device may simply left proximate the sterilizer for use by any of the numerous staff who have cause to use same.

Secondly, there is a risk that the openable capsule is not securely closed. This would allow the steam an easier path to the open end of the indicator tube within the capsule, and thus the device could give the false indication that the sterilizer was functioning satisfactorily.

Thirdly, steam has a propensity to condense on the external, and more importantly the internal walls of the lumen. If sufficient steam condenses of the internal wall of the lumen along the path to the capsule, there may be a plug of condensate which could prevent the steam from reaching the open ended indicator tube within the capsule.

Fourthly, the problem of condensation is also apparent when the lumen is removed after the test has been completed, and in some cases there can be a fine mist of water vapour or a fluid bubble retained within the lumen. When a subsequent test is conducted, the lumen is heated in the sterilizer and by means of conduction, this water vapour could also heat and be urged towards the chemical indicator within the capsule. The device could in this circumstance also provide false results.

Finally, it is contended by many of those in the art that the single narrow opening through which the steam passes before travelling the length of said lumen is too directionally sensitive, that is it does not provide a fair average of the steam penetration characteristics within the sterilization chamber.

Examples of directionally sensitive sterilization test devices are shown in consecutive published patent applications PCT/DE94/00687, PCT/DE94/00688, PCT/DE94/00689, all to Van Dijk Medezintechnik GmbH. All these documents disclose essentially cylindrical hollow test devices, one end of which is closed off from the atmosphere by means of a plug or stopper proximate to which a chemical indicator means is positioned in an inner chamber of the device, the alternate open end of the devices having different inserts provided therein to provide a penetrable barrier through which steam must pass to interact with the chemical indicator within the device.

In particular, PCT/DE94/00687 discloses the use of a threaded plug which is screwed into the open end of the device but which has threads of marginally lesser diameter than those provided internally of the device such that a helical channel is defined between the threads of the plug and those of the device. This device is effectively similar to the lumen device disclosed above, with the exception that a fixed helical path leads from the exterior of the device to the chemical indicator, as opposed to the spiral path along which the steam can travel within the lumen.

PCT/DE94/00688 discloses the use of an array of capillaries provided between the inner chamber of the device in which the indicator is located and the alternate open end of the device from which the steam within a sterilizer can penetrate, and PCT/DE94/00689 discloses the use of a porous material plug through which the steam can penetrate towards the indicator located in the inner chamber of the device. Neither of these latter two patent applications is specifically directed towards the use of a so-called "tortuous path" such as is provided by the helical path disclosed in PCT/DE94/00687 or the spiral path along which the steam travels in the lumen of the abovementioned current devices, whereas PCT/DE94/00687 does not consider the use of a so-called "porous load".

Additionally, all the devices disclosed in the abovementioned patent applications are directionally sensitive in that steam can only begin to penetrate either the tortuous path or the porous load (or equivalent load) from one particular side, and furthermore only on one particular surface of the device. It is to be mentioned that the conditions within autoclave units in general are extreme and nonuniform, and it is possible that the directional sensitivity, which term is used to describe the generally linear path along which the steam or other sterilant travels before coming into contact with the indicator, of such devices can result in the device producing false results.

It is an object of the present invention to provide a sterilizer test device which at least mitigates if not eradicates the disadvantages of the prior art devices, and which is furthermore reusable and combines the advantageous qualities of the devices mentioned.

According to the present invention there is provided a sterilizer test device comprising a pair of bodies releasably and sealably connected together defining an internal primary chamber within the device to which access is gained by disconnecting said bodies, at least one of said bodies being essentially comprised of a porous element which allows penetration of steam therethrough and into said primary chamber, indicator means being provided between said bodies at some location within the primary chamber, said indicator means having a characteristic which changes while in the presence of steam and temperature after a predetermined time, characterised in that said porous element has one or more external surfaces through which steam can penetrate in a plurality of different directions.

Preferably intermediate tortuous path means is additionally provided internally of the device and sealingly divides the primary chamber into two secondary chambers, a first secondary chamber being defined between the tortuous path means and an inner surface of said at least one body through which steam having permeated said body emerges, and a second secondary chamber being defined to the alternate side of said tortuous path means from the first secondary chamber and having the indicator means disposed therein, said steam being constrained to flow into and around said tortuous path means before emerging into the second secondary chamber and thence coming into contact with the indicator means.

Preferably the said at least one body is provided with a substantially arcuate outer surface. In one embodiment, the said at least one body is preferably cylindrical.

Most preferably, the outer surface of the porous body is substantially continuous around at least one axis of the device.

It is most preferable that the two bodies connected together to form the device have a predetermined degree of porosity, and furthermore it is preferable that each of said two bodies is substantially hemispherical.

It is yet further preferable that at least one of the bodies is provided internally with a cavernous recess to increase the effective volume of the primary chamber.

It is further preferable that the porous bodies are manufactured from a sintered polypropylene material, which has the advantage that its porosity can be varied according to requirements of a particular device, and also that it can be formed in any desired shape. In an alternative embodiment, the porous bodies are manufactured from a spun bonded polymer material, but the manufacturing process for such materials is limited in that only articles having certain geometric shapes (such as a cylinder) can be produced because of the manner in which the polymeric material is spun.

It is yet further preferable that apertured diaphragm means is provided internally of the primary chamber substantially across the base of one of the said bodies thus defining a tertiary chamber with the surfaces of the cavernous recess in which steam having permeated the porous element from a plurality of different directions can collect before passing through said aperture into either the remainder of the primary chamber or the first secondary chamber.

It is also to be mentioned that such an apertured diaphragm could be used to sealingly divide either the first or second secondary chamber and thus define first and second tertiary chambers from said secondary chambers, and that two apertured diaphragms could be used to divide both the first and second secondary chambers as desired.

The division of the internal primary chamber into secondary and tertiary chambers has been shown experimentally to improve the overall performance of the sterilizer text device as a whole. Not wishing to be bound by theory, it is believed that this enhancement of performance is achieved because of the facility for steam to collect in the volume of the secondary and tertiary chambers in use which removes the effects on performance of the traditionally cyclical and intermittent operation of modern sterilizers, i.e. the alternate drawing of a vacuum and the introduction of steam into the sterilizer during use to substantially eliminate air.

In a further aspect of the invention there is provided a tortuous path means for use in a sterilizer test device of the type described above, said means comprising at least two substantially planar components having an outer surface and an inner surface separated by their thickness, said components being releasably connected together to bring their respective inner surfaces proximate one another, one or other or both of said components being provided with patterned grooved means on their inner surfaces following a labyrinthine, spiral or other tortuous path on said surface, one of said components being provided with an entry port leading from an outer surface of said component through the thickness thereof and opening at a particular location in said grooved means, characterised in that an intermediate member is sandwiched between the two components to sealingly close said grooved means and define a tortuous channel to at least one side of said intermediate member.

Preferably an exit port is also provided to allow fluid to escape from a particular location in the grooved means, or alternatively there is provided a recess in said inner surface of one of said components in which indication means as described above can be deposited.

Preferably the intermediate member is compressible to ensure sealing formation of said channel.

Preferably grooved means are provided on the inner surfaces of both components and the sandwiching of the intermediate member forms channels with each of said grooved means on either side of said member.

In a most preferred embodiment the components are hingedly connected over at a portion of their respective edges.

It is also preferable that the entry port of one component opens into the grooved means on the inner surface thereof proximate one end of said grooved means, and also that the exit port provided on the alternate component opens into the said grooved means in that component proximate one end thereof.

Most preferably, the intermediate member is secured to the hinged connection of the two components which ensures the correct positioning of said intermediate member when the said two components are releasably connected together.

It is yet further preferable that the intermediate member is provided with an aperture therein which links respective tortuous channels defined by said intermediate member on either side thereof.

In a yet further preferable embodiment, a chamber is defined internally of said tortuous path means in which steam can collect prior to being urged along said tortuous path.

It will be immediately understood by those skilled in the art that the provision of separable components having grooves brought together during the connection of the components to define respective channels with the intermediate compressible member allows for easy cleaning and airing of the grooved means. Hence, the device according to the invention can be both readily aired and cleaned while nevertheless being re-usable.

When the tortuous path means are used in connection with the sterilizer test device described above, the steam first permeates the porous bodies which substantially constitute the device and then is constrained to flow into a chamber of the device and thence through the tortuous path means before emerging therefrom into a further cavity in which is disposed the indicator means. The particular indicator means used is not important, and the device can be calibrated for use with a variety of different indicator types, such as chemical, biochemical, biological. It is also foreseen by the applicant that electronic sensing and detection apparatus may be used in place of the indicator means to provide accurate data logs on the characteristics of the atmosphere extant in the device in any of the chambers defined therein as a function of the time after the commencement of any particular sterilization sequence.

The fundamental advantages of the present invention are firstly that the use of cylindrical or hemi-spherical porous bodies to form the device allows steam to permeate into said bodies from any direction as substantially the entire surface of these bodies are porous, and secondly that the tortuous path means can be easily, simply, and quickly opened up to allow for airing and drying of the tortuous path. Thereafter both the test device and the tortuous path means can be reused. Obviously a quadrangular porous body having two or more of its external surfaces exposed to the steam to allow for penetration thereof would function in a similar manner.

A specific embodiment of the invention is now given by way of example with reference to the accompanying Figures wherein:

Figures 1, 1A:
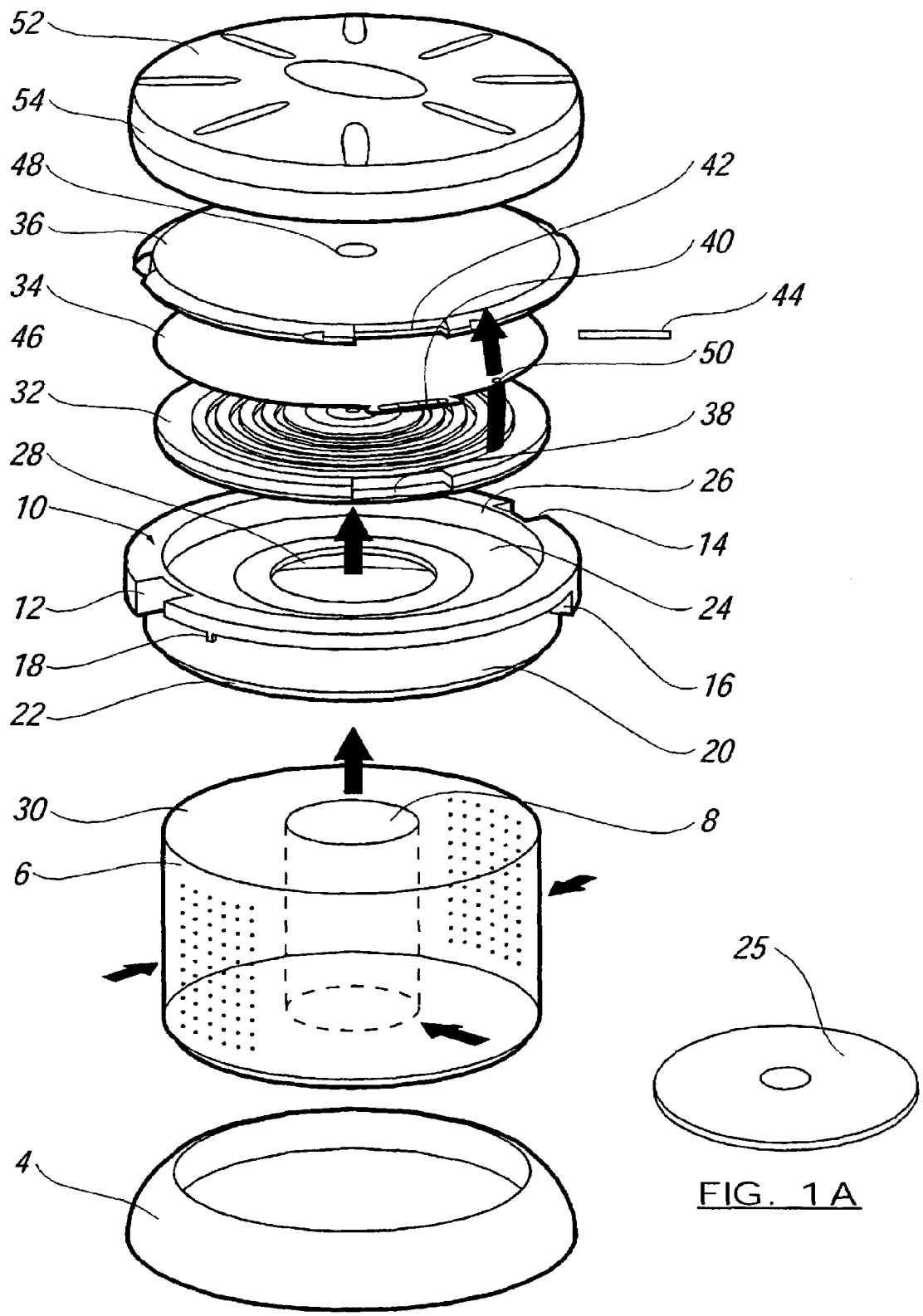
FIG. 1 shows an exploded perspective view of a cylindrical test device in accordance with the invention.
FIG. 1A shows a perspective view of an apertured diaphragm which may be used in conjunction with the invention.

Referring firstly to FIG. 1 there is shown a sterilizer test device indicated generally at 2 comprising an annular base 4 which on which the device stands when within a sterilizer, a cylindrical porous body 6 having a cavernous bore 8 provided therein of a depth less than that of the body 6 and chosen as required by the particular application. Above the body 6, a number of different components are provided to allow the device to function correctly. The first of these is an annular cap 10 having formations 12, 14, 16, 18 which permit the rotating locking connection of other components above said cap.

It will be seen from the diagram that the cap 10 is provided both with a collar 20 which is chamfered around its outer surface shown at 22 and is marginally greater in diameter than the body 6 over which it is disposed. An annular inner surface 24 is provided at approximately the median of the depth of the cap, and above and around the periphery of said surface 24 there is provided an annular skirt 26 which defines a circular recess with the said surface 24. An aperture 28 allows steam which has permeated through the porous body 6 to pass from the upper surface 30 thereof and from within the cavity 8 through the cap 10.

The apertured diaphragm 25 may be sealingly disposed either on the inner surface of the body 6 over the cavernous bore 8 or in the aperture 28 so that a tertiary chamber is defined by said diaphragm and said cavernous bore internally of the body, as this has experimentally shown to improve the performance of the device, that is to more accurately determine if a particular sterilizer under test is efficacious.

In accordance with the invention there is provided a tortuous path device consisting of three components 32, 34, 36 which are hingedly connected together around their circumferences at hinge means 38, 40, 42 respectively. Specifically, the hinge means 38 is a protrusion, 40 is an aperture of marginally greater size than said protrusion and through which said protrusion is fed before locating in a recess 42 in the component 36 in which it is pinned by means of rod 44.

With specific regard to said components 32, 34, 36, the first and third components 32, 36 are substantially planar and provided with spiral grooves 46 in one surface (only shown in respect of component 32). The second component 34 is an intermediate component ideally of a compressible material which is sandwiched between components 32, 36 on releasably connecting same together and ideally sealingly forms spiral channels with the said grooves provided in the surfaces of the first and third components on either side thereof.

The first and third components 32, 36 are provided with apertures (one of which is shown at 48 in the component 36) at their centres which form entry and exit ports to the spiral channels formed between said components. The intermediate component 34 is additionally provided with an aperture 50 which allows fluid communication between the channel formed in the component 32 on one side of component 34 and channel formed in component 36. Thus the fluid enters the spiral channel formed in the first component through the aperture in said component 32 at its centre, and is subsequently constrained to spiral outwardly from said centre until reaching the aperture 50 (which is ideally located at the end of the spiral groove 46). The fluid can then move through the aperture 50 and into the second spiral channel and wherein it is constrained to spiral inwardly towards the aperture 48 from which it ultimately emerges.

The entire arrangement of the tortuous path device (32, 34, 36) is received in the upper recess defined in the cap 10 by the surface 24 and its peripherally surrounding skirt 26 and optionally locked therein behind suitable flanges provided on the skirt 26. As the device 2 is assembled, the pre-assembled tortuous device (32, 34, 36) may be simply dropped into said recess and rotated by means of thumb indentations (not shown) provided on the upper surface of component 38.

Once secured in place, an indicator (not shown or described in this application as being considered beyond the scope hereof) is positioned above the aperture 48, and a lid 52 having depending skirt 54 is secured to the device by interengagement of formations (not shown) provided on the inner surface of said skirt 54 with the formations 12, 14, 16, 18 provided on the cap 10. The device is then placed in a sterilizer which is then activated, and after a conventional sterilization operation is complete the device is removed and opened for inspection of the indicator.

It is to be mentioned that the device may be inverted, the base 4 dispensed with, and the lid 52 may be suitably designed to function as a base having an inner surface in which an indicator may be disposed. In terms of the wording of the claims appended hereto, the primary chamber internally of the device is defined by the cavernous bore 8 and the inner surface of said lid 52 through the aperture 28. This chamber is sealingly divided by the interposing of the tortuous path means (32, 34, 36) on either side of which are defined first (on the side of the cavernous bore 8) and secondary (on the side of the lid 52 inner surface) chambers. The first secondary chamber may again be divided by the interposing of the apertured diaphragm 25 as previously mentioned so that a tertiary chamber is defined within the body 6 by said cavernous bore 8 and said diaphragm.

It is also to be mentioned that the device described with reference to FIG. 1 can be used as a sterilizer test device without the tortuous path means described above. An indicator may simply be placed on the annular surface 24 or within the lid 52 to which steam can gain access after having first permeated the porous body 6.

Additionally the configuration of the device 2 is adapted to be further modified so that the porous body can be removed leaving only the base 4, cap 10, tortuous path means (32, 34, 36) and lid 52.

However, use of the complete device having both porous body and tortuous path means is preferred.

Figure 2:
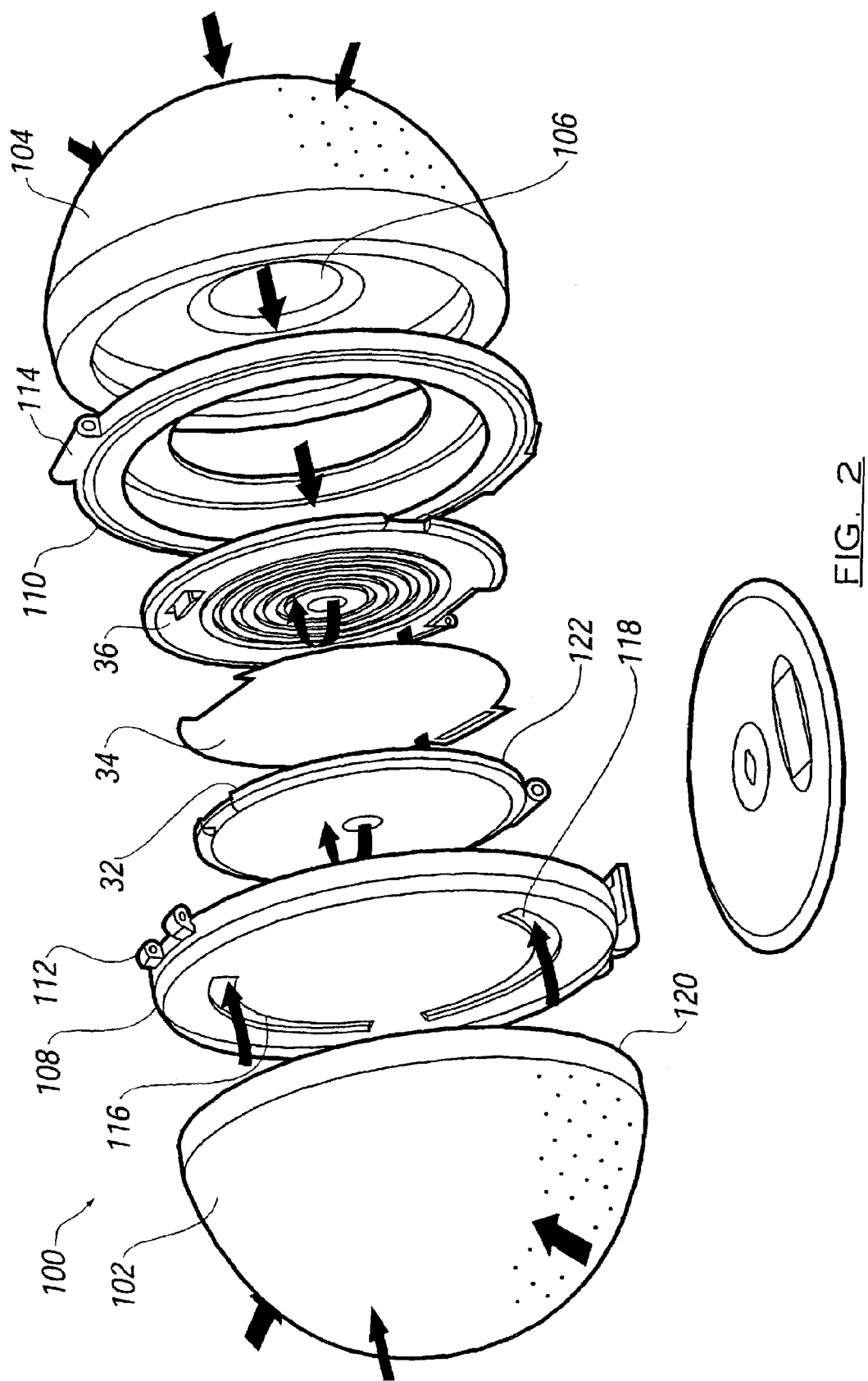
FIG. 2 shows an exploded perspective view of a spherical test device in accordance with a different embodiment of the invention.

Referring now to FIG. 2 there is shown a modified configuration of sterilizer test device 100. The device comprises of a tortuous path device (32, 34, 36) as hereinbefore described disposed internally of the device, and two hemispherical porous bodies 102, 104. Body 104 is provided internally with a cavity 106 in which steam may collect, and the portions of both bodies 102 proximate their diametral planes are received in the hingedly connectable skirt members 108, 110 having hinge formations shown at 112, 114.

As with the embodiment shown in FIG. 1, a suitably sized apertured diaphragm may be used to define a chamber with said cavity 106 as previously discussed.

The skirt member 108 is provided with a plurality of slots 116, 118 through which steam emerging from the planar surface 120 of body 102 can pass. When assembled together, the configuration is such that steam permeating through the body 102 passes to the outside of the tortuous path device and towards and into the cavity 106 without coming into contact with the indicator (not shown) which is disposed between the outer surface of the component 32 and the rear surface 122 of the cap 108. The disposition of said indicator, possibly within a recess defined in said rear surface 122, and the clamping arrangement of the two caps on the tortuous path device (32, 34, 36) thereover ensures that steam cannot adversely affect the indicator such that the device would give rise to false results.

In a similar manner to the operation of the device shown in FIG. 1, the device 100 can be easily and quickly opened and the tortuous path device released from over the indicator which can then be inspected to ensure that a sterilizer is functioning correctly. Additionally, the tortuous path device can be removed quickly, and opened for drying and cleaning.

It is to be mentioned that the various arrows provided on the diagrams are indicative of the possible flow of steam from outside the devices and the particular flow paths possible inside said device. It is most important to note that both the devices disclosed herein are both reusable and "directionless" in that steam drawn towards the devices when inside an operative sterilizer can permeate through the porous body as soon as it comes into contact therewith. This is in sharp distinction to the currently available devices which are either not reusable or which although being of similar size and shape to the devices described herein, generally provide only a few discrete ports through which access to a porous medium is contained. Such devices are heavily directional, and therefore disadvantaged in comparison to the present invention.

The invention claimed is:

1. A sterilizer test device comprising:
   at least a pair of bodies releasably and resealably connected together defining an internal primary chamber within the device to which access is gained by disconnecting said bodies, at least one of said bodies being comprised of a porous element which allows penetration of steam there through and into said primary chamber, wherein said porous element has one or more porous and external surfaces that are substantially arcuate in form, or two or more porous and external surfaces, whereby steam can penetrate said porous element from a plurality of different directions;
   indicator means being provided between said bodies at some location within the primary chamber, said indicator means having a characteristic which changes while in the presence of steam and temperature after a predetermined time; and
   tortuous path means provided internally of the device, sealingly dividing the primary chamber into two secondary chambers, a first secondary chamber being defined between the tortuous path means and an inner surface of said at least one body through which steam having permeated said body emerges, and a second secondary chamber being defined to the alternate side of said tortuous path means from the first secondary chamber and having the indicator means disposed therein, the tortuous path means having a single entry port in communication with the first secondary chamber and a single exit port in communication with the second secondary chamber, said steam being substantially constrained to flow from the first secondary chamber through the single entry port into and around said tortuous path means and then through the single exit port before emerging into the second secondary chamber.

2. A device according to claim 1 wherein the one or more porous and external surfaces are substantially arcuate in form.

3. A device according to claim 2 wherein said at least one body is cylindrical.

4. A device according to claim 2 wherein said at least one body is at least partially spherical.

5. A device according to claim 2 wherein the one or more porous and external surfaces of the porous element are substantially continuous around at least one axis of the device.

6. A device according to claim 1 wherein the pair of bodies connected together to form the device both have a predetermined degree of porosity.

7. A device according to claim 1 wherein each of the pair of bodies is substantially hemispherical.

8. A device according to claim 1 wherein at least one of the bodies is provided internally with a cavernous recess to increase the effective volume of the primary chamber.

9. A device according to claim 8 further comprising apertured diaphragm means provided to sealingly define a tertiary chamber within the device in which steam can collect.

10. A device according to claim 1 wherein the pair of bodies are manufactured from a sintered polypropylene material.

11. A device according to claim 1 wherein the device is reusable upon replacement of the indicator means.

12. A device according to claim 1 wherein the porous element has two or more porous and external surfaces.

13. A device according to claim 1 wherein the porous element comprises substantially the entire surface on one or both of said bodies.

14. A sterilizer test device comprising:

at least a pair of bodies releasably and resealably connected together defining an internal primary chamber within the device to which access is gained by disconnecting said bodies, at least one of said bodies being comprised of a porous element which allows penetration of steam therethrough and into said primary chamber, wherein said porous element has one or more porous and external surfaces that are substantially arcuate in form and substantially continuous around at least one axis of the device, whereby steam can penetrate said porous element from a plurality of different directions;

indicator means being provided between said bodies at some location within the primary chamber, said indicator means having a characteristic which changes while in the presence of steam and temperature after a predetermined time; and tortuous path means provided internally of the device, sealingly dividing the primary chamber into two secondary chambers, a first secondary chamber being defined between the tortuous path means and an inner surface of said at least one body through which steam having permeated said body emerges, and a second secondary chamber being defined to the alternate side of said tortuous path means from the first secondary chamber and having the indicator means disposed therein, the tortuous path means having a single entry port in communication with the first secondary chamber and a single exit port in communication with the second secondary chamber, said steam being substantially constrained to flow from the first secondary chamber through the single entry port into and around said tortuous path means and then through the single exit port before emerging into the second secondary chamber.

\* \* \* \* \*

UNITED STATES PATENT AND TRADEMARK OFFICE
CERTIFICATE OF CORRECTION

PATENT NO.       : 7,608,219 B2
APPLICATION NO. : 10/182213
DATED            : October 27, 2009
INVENTOR(S)      : Richard Bancroft It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 796 days.

Signed and Sealed this

Twelfth Day of October, 2010

David J. Kappos
*Director of the United States Patent and Trademark Office*